US009629896B2

(12) United States Patent
Andreelli et al.

(10) Patent No.: US 9,629,896 B2
(45) Date of Patent: Apr. 25, 2017

(54) COMPOSITION INCLUDING THE HIP/PAP PROTEIN OR ONE OF THE DERIVATIVES THEREOF FOR TREATING INSULIN RESISTANCE

(71) Applicants: ALFACT INNOVATION, Paris (FR); INSERM (INSTITUT NATIONAL DE LA SANTÉ ET DE LA RECHERCHE MÉDICALE), Paris (FR)

(72) Inventors: Fabrizio Andreelli, Levallois Perret (FR); Paul Amouyal, Sevres (FR); Christophe Magnan, Paris (FR); Celine Cruciani-Guglielmacci, Montesson (FR); Jamila Vaivre, Paris (FR); Marion Darnaud, Paris (FR); Laure Jamot, Paris (FR); Christian Brechot, Paris (FR); Gilles Amouyal, Paris (FR)

(73) Assignees: ALFACT INNOVATION, Paris (FR); INSERM (INSTITUTE NATIONAL DE LA SANTE ET DE LA RECHERCHE MEDICALE), Paris (FR); UNIVERSITE PARIS SUD, Orsay (FR); UNIVERSITE PARIS DIDEROT—PARIS 7, Paris (FR)

( * ) Notice: Subject to any disclaimer, the term of this patent is extended or adjusted under 35 U.S.C. 154(b) by 0 days.

(21) Appl. No.: 14/783,625

(22) PCT Filed: Apr. 4, 2014

(86) PCT No.: PCT/FR2014/050821
§ 371 (c)(1),
(2) Date: Oct. 9, 2015

(87) PCT Pub. No.: WO2014/167230
PCT Pub. Date: Oct. 16, 2014

(65) Prior Publication Data
US 2016/0058833 A1    Mar. 3, 2016

(30) Foreign Application Priority Data
Apr. 10, 2013 (FR) .................................... 13 53245

(51) Int. Cl.
*A61K 38/17* (2006.01)
*A61K 38/00* (2006.01)

(52) U.S. Cl.
CPC ........ *A61K 38/1709* (2013.01); *A61K 38/005* (2013.01)

(58) Field of Classification Search
CPC .......................... A61K 38/1709; C07K 14/47
See application file for complete search history.

(56) References Cited

U.S. PATENT DOCUMENTS

| | | | | |
|---|---|---|---|---|
| 2003/0212000 | A1* | 11/2003 | Van Antwerp | A61K 38/1709 514/7.6 |
| 2011/0144036 | A1* | 6/2011 | Christa | A61K 38/1709 514/21.2 |
| 2015/0174111 | A1* | 6/2015 | Levetan | A61K 31/4439 514/6.7 |

FOREIGN PATENT DOCUMENTS

| | | |
|---|---|---|
| EP | 2 260 857 A1 | 12/2010 |
| WO | WO 2006/096565 A2 * | 9/2006 |
| WO | 2006/128083 A2 | 11/2006 |

OTHER PUBLICATIONS

Okamoto et al.; "The Reg gene family and Reg proteins: with special attention to the regeneration of pancreatic Beta-cells"; Journal of Hepato-Biliary-Pancreatic Surgery, vol. 6, No. 3, Jan. 1, 1999, pp. 254-262.
Rosty et al.; "Identifaction of Hepatocarcinoma-Intestine-Pancreatitis-associated Protein I as a Biomarker for Pancreatic Ductal Adenocarcinoma by Protein Biochip Technology"; Cancer Research, vol. 62, No. 2, Mar. 15, 2002, pp. 1868-1875.
Ogawa et al.; "Increased Expression of HIP/PAP and Regenerating Gene III in Human Inflammatory Bowel Disease and a Murine Bacterial Reconstitution Model"; Inflammatory Bowel Diseases, vol. 9, No. 3, May 1, 2003, pp. 162-170.
Graf et al.; "Exocrine Meets Endocrine: Pancreatic Stone Protein and Regenerating Protein—Two Sides of the Same Coin"; Journal of Surgical Research, vol. 133, No. 2, Jun. 15, 2006, pp. 113-120.
Zhang et al.; "Reg gene family and human diseases", World Journal of Gastroenterology, vol. 9, No. 12, Aug. 18, 2011, pp. 2635-2641.

* cited by examiner

*Primary Examiner* — Jeffrey E Russel
(74) *Attorney, Agent, or Firm* — Whitham, Curtis & Cook, P.C.

(57) ABSTRACT

The invention relates to a HIP/PAP protein or to one of the derivatives thereof for use thereof for treating or preventing insulin resistance in non-insulin dependent subjects.

15 Claims, 3 Drawing Sheets

COMPOSITION INCLUDING THE HIP/PAP PROTEIN OR ONE OF THE DERIVATIVES THEREOF FOR TREATING INSULIN RESISTANCE

PRIOR ART

The present invention relates to the use of the HIP/PAP protein or one of the derivatives thereof, for reducing insulin resistance or preventing the development thereof. The invention will be particularly intended for non-insulin-dependent patients.

Insulin resistance is defined by a decrease in the metabolic effects of insulin on insulin-sensitive tissues (skeletal muscles, white adipose tissue, liver). In practice, insulin resistance (IR) manifests itself through an inability of insulin to inhibit hepatic glucose production (via the inhibition of neoglucogenesis or of glycogenolysis), through a decrease in the capacity of muscle tissue to take up and therefore to use glucose, and through exaggerated lipolysis of white adipose tissue leading to an elevated plasma concentration of free fatty acids.

Insulin sensitivity (or conversely insulin resistance) along with insulin secretion are two dependent variables which interact in concert to maintain glycemic homeostasis. Any modification of glycemia leads to a modification of insulinemia and vice-versa. Consequently, any increase in insulin resistance is compensated for by a concomitant increase in insulin secretion (compensatory hyperinsulinemia is then observed) so as to maintain normal glycemia (normoglycemia) or to limit progression toward hyperglycemia (i.e. to avoid pathological escalation of normal glycemic tolerance toward moderate fasting glycemia or glucose intolerance). Starting from a certain threshold, the progression of IR leads to a phenomenon of escape due to exhaustion of the pancreatic beta insulin secretory function, the underlying mechanisms of which are still complex (functional and structural loss of mitochondrial function and/or apoptosis of beta-pancreatic cells, in particular associated with glucotoxicity). There is then a clear increase in glycemia (fasting glycemia 1.26 g/l, i.e. 7 mM), and the term diabetes is used. It is considered that type II diabetes has taken hold when the glycemia exceeds this fasting threshold of 7 mM twice on a venous blood sample. This reflects the non-compensation of the IR by insulin secretion, attesting to the existence of "relative" insulinopenia. At this stage, it may be necessary to initiate insulin therapy as a supplement to treating the IR, by means of health and dietary measures, or pharmacological treatments. At an advanced stage, since glucose-dependent insulin secretion becomes too low (or even virtually zero), it then becomes imperative to set up multi-injection insulin therapy (see Silvio E et al., *Diabetes Care* 35:1364-1379, 2012; Management of Hyperglycemia in Type 2 Diabetes: A Patient-Centered Approach. Position Statement of the American Diabetes Association (ADA) and the European Association for the Study of Diabetes (EASD)).

Insulin is assayed in humans using a radioimmunological, or ELISA, method, under fasting conditions, on plasma or serum. The normal (fasting) basal values range from 3.2 to 16.3 mIU/l, then increase up to 40 mIU/l, as soon as the 20th minute after an oral glucose load of 75 g, and return to basal values two hours after the glucose ingestion. This measurement combined with that of the glycemia makes it possible to estimate the capacity of the insulin to promote tissue glucose uptake and to thus maintain a normal carbohydrate homeostasis.

Insulin sensitivity (and also the pancreatic β secretory function which correlates therewith) may be estimated using the HOMA calculator software (v. 2.2.2, Diabetes trials Unit, University of Oxford, downloadable from the following address: www.dtu.ox.ac.uk/homacalculator/download.php) recently refined to HOMA2(Homeostatic Model Assessment). The HOMA 2 model (Levy JC et al., *Diabetes Care*, 1998; 21: 2191-2192, see also Wallace TM, Levy JC, Matthews DR. *Diabetes Care*, 2004; 27(6): 1487-95) is a structural computer model, the calculator of which is based on the glucose/insulin regulation loop, and makes it possible to determine, from measurements of fasting plasma concentrations of glucose and of insulin (or of C-peptide), the pancreatic beta function (% β, i.e. HOMA B) and the insulin sensitivity (% S) of an individual, since, for each combination of % βand of % S, there is only one corresponding combination of glucose and insulin/C-peptide. The validation of this calculator has been carried out by comparing the equations used to the values obtained by direct measurement of insulin sensitivity and of insulin secretion using invasive methods reserved for research (hyperinsulinemic-euglycemic clamp or hyperglycemic clamp methods). The calculator makes it possible to estimate both the insulin sensitivity and insulin secretion by means of fasting blood samples.

It has been shown (Kahn S E et al., *Diabetes* 1993) that, in a subject with a normal carbohydrate tolerance and variable degrees of obesity or of insulin resistance, the β secretory function varies quantitatively with the insulin sensitivity. There is in fact a hyperbolic relationship between insulin sensitivity (S) and β function (β). The product of the value of the y-axis (β) multiplied by the value of the x-axis S is a constant which corresponds to the carbohydrate tolerance of the subject.

Thus, it is possible to estimate the insulin resistance by calculating the HOMA-IR index (Matthews et al., 1985), according to the following formula: [(Insulinemia$_{fasting\ (\mu U/ml)}$×Glycemia$_{fasting\ (mM)}$)/22.5]. In a healthy, non-insulin-resistant subject, the fasting HOMA-IR index is generally close to 1.

Finally, it is possible to perform an insulin tolerance test (ITT), which consists in monitoring the glycemia after having injected (peritoneally, intravenously or subcutaneously) a dose of fast-acting insulin calculated relative to the body weight (generally 0.75 IU/kg of body weight). This technique is especially carried out in animals. In humans, in order to dispense with the difficulties and risks associated with hypoglycemia, several adjustments have been proposed, defining a modified insulin tolerance test or short intravenous test. The interpretation relates only to the rate of glycemia decrease over the course of the first fifteen minutes of the test, with determination of the [(Basal glycemia$_{G0}$−Glycemia at 15 minutes$_{G15}$)/G0] ratio. This ratio is normally less than 0.5 in healthy, non-insulin-resistant patients.

The serum C-peptide concentration is a mark of insulin secretion and reflects the capacity of the pancreatic beta cells to produce insulin. The normal fasting values range from 0.27 to 1.43 nmol/l (or from 0.8 to 4.2 ng/ml) in humans. In a subject with type I diabetes or type II diabetes with pancreatic cell involvement, the C-peptide level is decreased. In patients who have insulin resistance associated with endogenous hyperinsulinemia, this level is increased compared with the normal.

There are numerous possible etiologies of insulin resistance and they result from several, possibly combined, abnormalities: abdominal excess weight, or visceral obesity, a prolonged sedentary nature or physical inactivity, genetic or acquired abnormalities affecting the function of insulin post-receptor signaling cascade proteins, an excess of counter-regulatory hormones, ovarian dysfunction, various pharmaceutical agents (for instance corticotherapies, abuse of sex steroids), gestation, hypercatabolism situations, undernourishment, a low birth weight for the size and/or fetal malnutrition. It has been shown in particular that obesity is a major factor of IR and that the latter increases when the body mass index (BMI) increases. In particular, IR is virtually certain when the BMI exceeds 40 kg/m$^2$ (Mericq et al.). In addition, it has been shown that the distribution of excess fat body mass also plays a role in the setting up of IR. Indeed, abdominal (or truncal or visceral) obesity is recognized as fundamental in the physiopathology of IR on the whole-body scale. This explains the possibility of being insulin resistant for BMIs much lower than 40 kg/m$^2$, or even in overweight values in subjects, if the excess of fat body mass is abdominal. Patients who have had a cardiovascular event (myocardial infarction, ischemic stroke, arteriopathy of the lower limbs), which leads to the discovery of the up until then unknown insulin resistance state, fall within this category. Indeed, these populations suffering from insulin resistance are at high risk of the occurrence of a cardiovascular event independent of the conventional risk factors (high LDL-cholesterol, smoking, arterial hypertension, type 2 diabetes). The occurrence of a cardiovascular event in this population must bring about the diagnosis of insulin resistance in order to treat it therapeutically. Most situations where insulin resistance is present have in common a modification of fat body mass storage distribution. The adipose tissue in fact plays an important role in the storage of energy excess originating from foods in the form of fatty acid. Its increased mass in obesity reduces glucose uptake and increases lipolysis. In subjects predisposed to IR, a development of intra-abdominal adipose tissue is observed. Said tissue is itself less sensitive than subcutaneous adipose tissue in terms of the effect of inhibition of lipolysis by insulin. Consequently, the visceral adipose tissue has increased lipolytic capacities. The fatty acids released in excess and in a poorly regulated manner are recovered by the peritoneal circulation and then the portal vein and then by the liver. These fatty acid affluxes participate to a large extent in the physiopathology of non-alcoholic hepatic steatosis in insulin-resistant subjects. The steatotic liver partly exports the stored lipids in the form of triglycerides (VLDL-triglyceride particles) in the blood stream. These triglycerides may then be hydrolyzed by endothelial lipoprotein lipase (LPL), thereby making it possible for the skeletal muscles and the pancreatic islets to take up these fatty acids. Multi tissue deposits of ectopic lipids, which themselves participate in reducing the effect of insulin and/or in reducing insulin secretion, thus appear.

IR is therefore associated with various pathological conditions such as dyslipidemias and/or arterial hypertension. The phenotype associated with IR is thus considered to be a central player in the development of atheromatous cardiovascular diseases.

Insulin resistance now represents a therapeutic target in its own right. Thus, in the context of the risk of occurrence of a cardiovascular event, while it is recommended to control the conventional cardiovascular factors (arterial hypertension, atherogenic dyslipidemia, smoking, type 2 diabetes), it is also increasingly indicated to intervene directly on insulin resistance.

In addition, it is currently considered that chronic hyperinsulinism caused by IR may promote cell mitogenesis, explaining a super risk of occurrence of cancers in insulin-resistant populations.

It therefore appears to be fundamental to develop therapeutic tools which make it possible to specifically target insulin resistance, and not insulinopenia and/or functonal pancreatic beta deficiencies, for treating patients, in particular upstream of type II diabetes, and more particularly non-insulin-dependent patients.

The known oral antidiabetics, such as hypoglycemic sulfamides or sulfonylureas and glinides, act exclusively on the beta cells of the endocrine pancreas by stimulating insulin secretion, but they have no direct effect on insulin sensitivity.

Compounds are currently known which make it possible to specifically reduce insulin resistance (without effect on insulin secretion), such as thiazolidinediones, or glitazones, or else, to a lesser extent, metformin, which act respectively on adipose and hepatic insulin resistance. Nevertheless, their use is difficult because of the considerable side effects or the difficulty in using them in certain patients (digestive intolerance, pregnancy, renal or cardiac or hepatic failure, etc.).

There is therefore a need for novel compounds for treating, decreasing or preventing insulin resistance in non-insulin-dependent or non-insulinopenic patients, this being all the more so since the glitazone class is no longer sold in France, reducing the class of insulin-sensitizing hypoglycemic drugs to only metformin.

The applicant has demonstrated that, surprisingly, the HIP/PAP protein makes it possible to specifically decrease insulin resistance. The HIP/PAP protein may therefore advantageously be used for treating, limiting or preventing IR and the associated symptoms and disorders, in particular in non-insulin-dependent patients.

The HIP/PAP protein is known for its anti-apoptotic and mitogenic activity on hepatic cells (US 13/032,521, WO 2004/112824, Simon et al., *FASEB J.* 2003 Aug.; 17(11): 1441-50).

It has also been shown that a 15-amino acid peptide, derived from the Reg IIIa family (HIP/PAP), the HIP (Human prolslet Peptide) peptide, has a regenerating activity on pancreatic islets and thus stimulates insulin production (US 2010/0093605). On the basis of these results, the use of said peptide and of derivatives of proteins of the Reg IIIa family for treating strictly insulin-dependent patients (suffering from type I diabetes or who have decompensated type II diabetes) has been suggested.

To the applicant's knowledge, no prior art document describes the effect of the HIP/PAP protein on insulin resistance, for its use in non-insulin-dependent subjects.

SUMMARY OF THE INVENTION

The present invention thus relates to the HIP/PAP protein, or one of the derivatives thereof, for use thereof, in non-insulin-dependent subjects, for treating or preventing insulin resistance, and in particular for limiting and/or reducing insulin resistance or for preventing its appearance in populations at risk. A subject of the invention is thus in particular the HIP/PAP protein, or one of the derivatives thereof, for its use in non-insulin-dependent subjects, for treating or preventing insulin resistance of peripheral tissues.

According to various embodiments, the target subjects of the invention have a pancreatic β function (% β, i.e.: HOMA B), estimated on the basis of the HOMA 2 model, of greater than or equal to 60% and/or a HOMA-IR of less than 6.

In particular, the HIP/PAP protein, or one of the derivatives thereof, may be intended for subjects with a fasting glycemia of less than 125 mg/dl, in particular less than 120 mg/dl and more particularly less than 110 mg/dl.

In certain embodiments, the subjects have, 2 h after an oral glucose tolerance test, a glycemia of less than 200 mg/dl, in particular less than 180 mg/dl and more particularly less than 140 mg/dl.

In certain embodiments, the subjects have a normal carbohydrate tolerance and/or have a normal fasting glycemia.

The present invention will also find applications for increasing muscle development, stimulating increased lean body mass and preventing or limiting muscle catabolism and protein undernourishment, for preventing or treating dyslipidemia and in particular hypercholesterolemia, and for preventing or treating atherosclerosis, in particular coronary or cerebral artery disease, and arteriopathy of the lower limbs.

Thus, the invention will also be advantageously intended for subjects having at least one of the disorders chosen from visceral excess weight, obesity, metabolic syndrome, polycystic ovary syndrome, an eating disorder, hepatitis C, hepatic steatosis and sarcopenia, and more particularly for subjects having at least one disorder chosen from the group consisting of visceral excess weight, obesity, hyperandrogenism, an eating disorder, sarcopenia, hypercatabolism and undernourishment.

The HIP/PAP protein, or one of the derivatives thereof, according to the invention is also intended for the treatment of insulin resistance associated with aging. In certain embodiments of the invention, the non-insulin-dependent subject is therefore an elderly subject.

In certain embodiments, the derivatives of the HIP/PAP protein are characterized in that they comprise an amino acid sequence having a sequence identity of at least 90% with the polypeptide consisting of the amino acid sequence chosen from the sequences SEQ ID Nos 1 to 4. The sequence of said derivatives differs from the sequence SEQ ID No. 4 by at least one amino acid.

Finally, the invention relates to a composition comprising an effective amount of the HIP/PAP protein or of one of the derivatives thereof, as defined according to the present invention, as a mixture with at least one physiologically acceptable excipient, for its use for treating or preventing insulin resistance in non-insulin-dependent subjects.

The compositions according to the invention may comprise an effective amount of the HIP/PAP protein or of one of the derivatives thereof, in combination with another active agent for regulating glycemic homeostasis.

The various embodiments of the invention may optionally be taken in combination with one another.

DETAILED DESCRIPTION OF THE INVENTION

The applicant has demonstrated that the administration of the HIP/PAP protein to subjects who are non-insulin-dependent, but have carbohydrate homeostasis disorders, leads to a very significant decrease in the HOMA-IR index and also an increase in the hypoglycemic effect of exogenous insulin, thereby resulting in a greater drop in the glycemia, after intraperitoneal administration of fast-acting insulin during an insulin tolerance test (or ITT). This effect suggests that the administration of the HIP/PAP protein leads to a specific reduction in insulin resistance. These effects are not accompanied by an increase in insulin secretion, neither at the basal level, nor during OGTT tests. These results thus illustrate a specific effect of the HIP/PAP protein on the decrease in insulin resistance (or on the increase in insulin sensitivity) and not on insulin secretion.

Subject Categories and a Therapeutic Application of the Invention:

The present invention relates to the HIP/PAP protein, or one of the derivatives thereof, for its use for treating or reducing insulin resistance, and the resistance of peripheral tissues, or preventing, limiting or preventing their development (and conversely for increasing insulin sensitivity, or limiting or preventing a decrease in insulin sensitivity), in non-insulin-dependent subjects.

Advantageously, the HIP/PAP protein will also be used for stimulating or increasing tissue assimilation of glucose by target tissues.

According to the invention, the subjects consist of mammals, in particular of human beings, domestic and farm animals and also zoo animals and animals involved in sport, such as dogs, cats, horses, calves, cows, steers, pigs, rabbits, etc. More particularly, the present invention is intended for human beings. The values given in the present application, as a definition of the various parameters of the application, are provided with reference to the average values found in humans in good health.

The term "non-insulin-dependent subjects" is intended to mean a subject for whom the maintaining of glycemic homeostasis does not require the administration of insulin. More particularly, the non-insulin-dependent patients are not on any treatment with oral antidiabetics of the insulin-secretor family. By way of example, an insulin secretor comprises in particular hypoglycemic sulfamides or sulfonylureas and glinides. In such patients, in fact, the pancreatic beta secretory function is maintained (absence of endogenous insulinopenia), such that exogenous insulin therapy is not administered.

The invention comprises several embodiments defined below, which may be taken in combination with one another.

In particular, the invention is aimed at subjects who have a pancreatic β function (% β; i.e. HOMA B), estimated on the basis of the HOMA 2 model, of greater than or equal to 60%, in particular greater than or equal to 70%, greater than or equal to 75%, or greater than or equal to 80%. This value may not be greater than 100%. Such subjects also have an HOMA-IR of less than 6 and more particularly less than or equal to 5, in particular less than or equal to 4.5. According to the invention, the HOMA-IR index is also greater than or equal to 0.8 and in particular greater than or equal to 0.9. For example, the HIP/PAP protein may be administered to subjects having an HOMA-IR index ranging from 0.8 to 5, or else from 0.9 to 4.5, more particularly from 0.9 to 3.

The invention may thus be applied to individuals having a variable fasting glycemia of less than 126 mg/dl. In particular, the invention is not intended for diabetics.

The subjects of the invention may therefore have a normal glycemia (subjects who have a normal fasting glycemia), i.e. less than 110 mg/dl fasting, preferably less than or equal to 100 mg/dl, in particular ranging between 80 and 100 mg/dl, or else less than or equal to 95 mg/dl and in particular ranging from 80 to 95 mg/dl fasting. The subjects of the invention may, according to another aspect, have a moderate fasting hyperglycemia of less than 125 mg/dl fasting, in particular less than or equal to 120 mg/dl, in particular ranging from 110 to 125 mg/dl, more particularly from 110 to 120 mg/dl fasting.

In certain embodiments, the subjects of the invention, who have a moderate fasting hyperglycemia, may also be glucose intolerant and thus have, at the 2nd hour of an oral glucose load of 75 g, a glycemia of less than 200 mg/dl and in particular of between 140 and 200 mg/dl. For values of less than 140 mg/dl at the 2nd hour of the oral glucose load of 75 g, it is generally considered that the carbohydrate tolerance is normal.

The HIP/PAP protein for its use according to the invention will also be particularly intended for subjects as defined, at risk of developing insulin resistance, i.e. having, for example, at least one of the following pathological conditions favorable to the development of insulin resistance: excess weight, in particular visceral excess weight or obesity (in particular visceral obesity), a fat body mass distribution abnormality such as acquired or congenital, partial or generalized lipoatrophies, acquired or congenital, partial or total lipohypertrophies, fat body mass distribution abnormalities which are part of a genetic IR syndrome (such as Dunningan syndrome, Köbberling syndrome, Barraquer-Simons syndrome, Launsois-Bensaude syndrome or proximal symmetrical lipomatosis, Rabson-Mendenhall syndrome), hyperandrogenism, an eating disorder, a decrease in muscle mass and strength (in other words sarcopenia), a prolonged sedentary nature or physical inactivity, genetic or acquired abnormalities affecting the function of the proteins of the insulin post-receptor signaling cascade, an excess of counter-regulatory hormones, an ovarian dysfunction, various pharmaceutical agents (for instance corticotherapies or disruptions of endogenous cortisol secretion, abuse of sex steroids, antiretrovirals), a cardiovascular event revealing insulin resistance, a hypercatabolism situation, a low birth weight for the size and/or fetal malnutrition.

Visceral abdominal excess weight refers to a distribution of android type, in which the excess fat is located at the level of the abdominal organs, on the abdominal wall and sometimes on the upper back. Excess weight (or being overweight) and obesity are commonly defined by a body mass index (BMI), which takes into account the weight and the height of a subject in order to categorize the corpulence of the latter. Expressed in kg/m$^2$, the BMI corresponds to the weight divided by the square of the height. According to WHO standards, for an adult human being, a BMI of between 18.5 and 25 kg/m$^2$ corresponds to a "normal" corpulence, i.e. a corpulence not associated with an increase in the burden of morbidity (adverse effects on health). Excess weight is characterized by a BMI of between 25 and 30 kg/m$^2$, and obesity by a BMI of greater than 30 kg/m$^2$.

According to one preferred embodiment of the invention, the HIP/PAP protein will be used for preventing, in particular for reducing or limiting the development of insulin resistance, in non-insulinopenic and/or glucose intolerant and/or normoglycemic subjects. Such subjects may have at least one of the risk factors as reported above.

The applicant has also demonstrated that the HIP/PAP protein has a significant effect on dyslipidemias, and makes it possible in particular to reduce serum cholesterol and/or triglyceride concentrations in normal subjects, or in subjects whose weight is greater than the normal (excess weight or obesity). The HIP/PAP protein will thus advantageously be used in subjects exhibiting dyslipidemia and in particular hypercholesterolemia (serum cholesterol level greater than or equal to 2 g/l) and/or hypertriglyceridemia (serum triglyceride level greater than or equal to 2.3 mmol/l). The HIP/PAP protein will also be used according to the invention in patients who have experienced a cardiovascular event or who have atherosclerosis, coronary artery disease and/or arteriopathy of the lower limbs.

According to certain embodiments, the HIP/PAP protein according to the invention will thus be used for treating or reducing hyperlipemia, and in particular hypercholesterolemia, or for preventing or limiting their development.

More particularly, the use of the HIP/PAP protein or of one of the derivatives thereof according to the invention will make it possible to reduce serum LDL-cholesterol levels or to limit, reduce or prevent an increase therein. The HIP/PAP protein of the invention will also be suitable for the treatment and prevention of the associated pathological conditions such as atherosclerosis, coronary artery disease and arteriopathy of the lower limbs.

Finally, the applicant has demonstrated that the HIP/PAP protein leads, in normal subjects, as in subjects who are overweight and/or who have a high fat diet, to a decrease in the fat body mass/lean body mass ratio. More particularly, the treatment with the HIP/PAP protein leads, in individuals who are overweight and/or who have a high fat diet, to a significant decrease in the fat body mass, associated with a tendency toward an increased lean body mass. In normal subjects, the administration of HIP/PAP leads to a significant increase in the lean body mass associated with a tendency toward a decrease in the fat body mass. This effect is not associated with a weight loss. These results demonstrate that HIP/PAP influences energy metabolism and modifies the body composition by decreasing the fat body mass/lean body mass ratio in normal subjects as in subjects who are overweight. Finally, it has been shown that the HIP/PAP protein increases glucose assimilation specifically by the skeletal muscles, in particular in subjects who have a high fat diet and/or who are overweight.

The compositions of the invention are also particularly useful for treating or preventing insulin resistance of peripheral tissues. The term "peripheral tissues" is in particular intended to mean the liver, the adipose tissue and the skeletal muscle tissues. The increase in insulin sensitivity of these tissues results, inter alia, in an improvement in their capacity to assimilate glucose.

Increasing glucose assimilation in the muscles promotes muscle development. In addition, it is known that a decrease in the fat body mass/lean body mass ratio favorably influences the progression of pathological conditions of energy metabolism, such as metabolic syndrome, glucose intolerance, polycystic ovary syndrome, hyperandrogenism or diabetes. The invention thus also relates to the use of the HIP/PAP protein for decreasing the fat body mass/lean body mass ratio; it applies in particular in elderly subjects and/or subjects suffering from energy metabolism disorders and/or in subjects who are undernourished and/or who have sarcopenia and/or hypercatabolism and/or who have a significant surgical history (such as bariatric surgery and/or intestinal bypass and/or post-surgical reduction in exocrine secretion from the pancreas and/or intestinal resection and/or post-surgical need for feeding by artificial nutritional support). The term "elderly subject" is intended to mean in particular subjects over the age of 60 in particular, subjects over the age of 70 and more particularly subjects aged 75 and over. In these subjects, the HIP/PAP protein will also be useful for increasing anabolism and muscle development, preventing or treating undernourishment, in particular protein undernourishment, stimulating an increase in lean body mass and preventing and/or limiting muscle catabolism or sarcopenia, in particular in elderly subjects. Advantageously, the HIP/PAP protein or one of the derivatives thereof according to the invention will be used for treating, reducing or limiting muscle wasting or sarcopenia associated with aging in elderly subjects, or with protein undernourishment.

The HIP/PAP protein will also be advantageously used for treating or preventing undernourishment or hypercatabolism. For example, the HIP/PAP protein may be administered in undernourished subjects or in patients in a hypercatabolic state, or at risk of being so, independently of the BMI of the subjects, i.e. in subjects having a normal weight or exhibiting excess weight or obesity. Indeed, undernourishment also affects overweight or obese subjects.

The invention will therefore also be of interest for its use for treating insulin resistance associated with aging. The HIP/PAP protein according to the invention will thus be advantageously used in particular in elderly subjects, and/or for increasing muscle development, and/or stimulating an increase in lean body mass and/or preventing and/or limiting muscle catabolism and undernourishment, in particular protein undernourishment.

The HIP/PAP protein or one of the derivatives thereof may also be used in the form of a composition comprising an effective amount of said protein or of one of the derivatives thereof and at least one physiologically acceptable excipient.

According to certain embodiments of the invention, the HIP/PAP protein or one of the derivatives thereof may be administered in combination with at least one other therapeutic compound for treating insulin resistance or associated disorders.

The invention also relates to a method for treating insulin resistance in non-insulin-dependent subjects, comprising the administration of the HIP/PAP protein or one of the derivatives thereof.

Finally, the invention relates to the use of the HIP/PAP protein or one of the derivatives thereof, for producing a medicament for treating insulin resistance in non-insulin-dependent subjects.

HIP/PAP Protein and Derivatives According to the Invention:

The HIP/PAP protein according to the invention consists of the protein of sequence SEQ ID No. 4.

A derivative of the HIP/PAP protein according to the invention comprises a protein comprising or consisting of the amino acid sequence SEQ ID No. 1. The amino acid sequence SEQ ID No. 1 corresponds to the HIP/PAP protein of sequence SEQ ID No. 4, from which the N-terminal 26-amino acid signal peptide of said protein has been deleted.

According to another embodiment of the invention, a derivative of the HIP/PAP protein comprises the amino acid sequence SEQ ID No. 2 or consists of the amino acid sequence SEQ ID No. 2. The amino acid sequence SEQ ID No. 2 corresponds to the short form of the HIP/PAP protein and, compared with the amino acid sequence SEQ ID No. 1, has had the 11-amino acid propeptide in the N-terminal position deleted.

In one alternative embodiment, a derivative of the HIP/PAP protein comprises or consists of the sequence SEQ ID No. 3. The sequence SEQ ID No. 3 corresponds to the sequence SEQ ID No. 1, to which a methionine has been added in the N-terminal position. The HIP/PAP derivative of sequence SEQ ID No. 3 is more particularly illustrated in the examples and is also called rcHIP/PAP or ALF5755. This derivative may in particular be produced recombinantly in *E. Coli* cells. The 12-amino acid N-terminal propeptide (propeptide of 11 amino acids plus the additional methionine) may be cleaved, in order to obtain the short form of the HIP/PAP protein (SEQ ID No. 2).

According to the invention, the short or long forms of the HIP/PAP protein or of the derivatives thereof may be used indifferently.

The term "derivative of the HIP/PAP protein" is also intended to mean the biologically active derived forms of the HIP/PAP protein of sequence SEQ ID No. 4 or form from which the signal peptide has been deleted or short form, respectively of sequences SEQ ID No. 1 or 2. The term "biologically active" is intended to mean that the derivatives of the HIP/PAP protein have the same biological activity as the HIP/PAP protein or as the forms of sequences SEQ ID No. 1 or 2.

By way of example, a biologically active derivative of the HIP/PAP protein has, when it is administered in effective amount (see the protocols defined in the experimental section), at least one of the following activities:

Decrease in the HOMA-IR index during the OGTT test in ob/ob mice or mice having followed a high fat diet, as defined in the examples.

Decrease in glycemia during the glucose tolerance test, with respect to control animals.

Decrease in fat body mass and/or increase in lean body mass.

Increase in muscle absorption of glucose.

The invention also relates to the derivatives of the HIP/PAP protein according to the invention corresponding to a protein having at least 90% identity with a protein chosen from the group formed by the amino acid sequences of SEQ ID Nos 1 to 4.

It is understood that a protein having at least 90% identity with a reference protein will have at least 91%, 92%, 93%, 94%, 95%, 96%, 97%, 98% or 99% amino acid identity with said reference protein.

In order to determine the percentage identity of two amino acid sequences for the needs of the invention, the sequences will be aligned so as to allow an optimal comparison. Gaps may be introduced into one or other of the sequences to be aligned in order to enable optimal alignment, and the non-homologous sequences can be ignored for the comparison. The percentage identity of the two amino acid sequences compared may be obtained as described in the book by D. Voet and J. G. Voet, *Biochimie* (2nd Edition, De Boeck & Larcier, 2005, section 7.4, paragraph B). The alignments are carried out with the CLUSTAL W software (version 1.82) with the following parameters: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAPH DISTANCES="hide".

The biologically active derivatives of the HIP/PAP protein include the peptides comprising an amino acid sequence sufficiently homologous to the HIP/PAP protein or to one of the amino acid sequences SEQ ID Nos 1 to 4, which comprise the same number of amino acids as the corresponding reference sequence and which have the same biological activity.

The biologically active derivatives of the HIP/PAP protein also include the peptides comprising an amino acid sequence sufficiently homologous to the HIP/PAP protein or to one of the amino acid sequences SEQ ID Nos 1 to 4, which comprise a higher number of amino acids than the corresponding reference sequence and which have the same biological activity.

In addition to the natural allelic variants of the biologically active portion of the HIP/PAP protein which exist in mammals, those skilled in the art will understand that additional changes may be introduced via mutations into the sequences SEQ ID Nos 1 to 4, which do not modify the biological activity of said variants. In particular, substitutions of nonessential amino acids may be introduced into the sequences corresponding to the HIP/PAP protein or to the derivatives of sequences SEQ ID Nos 1 to 3. A "nonessential" amino acid is an amino acid which, when changed with respect to the reference sequence, and in particular with respect to the wild-type HIP/PAP protein (of sequence SEQ ID No. 4), does not modify the biological activity. In contrast, an "essential" amino acid consists of an amino acid which, when changed, modifies the biological activity of the protein or of the derived peptide.

In certain embodiments, the HIP/PAP protein, or one of the derivatives thereof, may be associated or combined by noncovalent bonds with non-HIP/PAP portions. For example, the HIP/PAP protein or one of the derivatives thereof could be associated with a liposome particle. Depending on the type of liposome, or on the production process, the HIP/PAP protein, or the derivative thereof, may be associated at the surface of the liposome or encapsulated inside said liposome.

The HIP/PAP protein, or one of the derivatives thereof, could also be associated with non-HIP/PAP portions by covalent bonds. Such non-HIP/PAP portions may be selected from protein or non-protein compounds, for example polyethylene glycol, thus forming a pegylated HIP/PAP derivative.

A derivative of the HIP/PAP protein according to the invention also comprises the derivatives which become biologically active only when they are administered to the patient.

Finally, the derivatives of the HIP/PAP protein also comprise chimeric proteins or fusion proteins. Such proteins are fused with non-HIP/PAP polypeptides. The latter may be fused with the N- or C-terminal part. Typically, the HIP/PAP protein or one of the derivatives thereof may be fused with the GST sequence at the level of their C-terminal part, in order to facilitate the purification of the recombinant proteins.

In certain embodiments of the invention, the HIP/PAP protein, or one of the derivatives thereof, is produced recombinantly in bacterial or animal cells, including insect and mammalian cells, according to techniques known to those skilled in the art.

In other embodiments, the HIP/PAP protein, or one of the derivatives thereof, as described above may be isolated from a cell or from a tissue by known purification techniques.

The HIP/PAP protein and the derivatives thereof may also be produced by chemical synthesis. In the remainder of the text, the term "HIP/PAP protein" will cover the HIP/PAP protein in itself, and also the derivatives thereof as described above.

Compositions According to the Invention:

The invention also relates to a composition comprising the HIP/PAP protein or one of the derivatives thereof as previously described, for its use for treating, reducing, limiting or preventing the development of insulin resistance in non-insulin-dependent patients.

Such a composition may also be used for increasing the lean body mass/fat body mass ratio in patients who have energy metabolism disorders.

According to various embodiments, the invention is particularly advantageous for treating subjects as previously defined.

Such a composition will comprise an effective amount of the HIP/PAP protein and at least one physiologically acceptable excipient, in particular a pharmaceutically acceptable excipient. The term "physiologically acceptable excipient" is intended to mean an excipient which is non-toxic to the subject to whom it is administered at the doses and concentrations used. The pharmaceutically acceptable excipients correspond to the excipients conventionally used by those skilled in the art in the context of pharmaceutical preparation. The excipients are chosen, according to the pharmaceutical form and the mode of administration desired, from the usual excipients which are known to those skilled in the art (see *Remington's Pharmaceutical Sciences*, $16^{th}$ edition, Osol, A ed., 1980).

By way of example, compositions according to the invention may comprise, according to the therapeutic indications and the HIP/PAP protein or the derivative thereof:

a) the HIP/PAP protein or one of the derivatives thereof;
b) a buffer capable of maintaining the pH in a maximum stability range, preferentially from 1 to 9, more particularly from 4 to 8 and even more particularly from 6 to 7.5;
c) a detergent or a surfactant which stabilizes the protein or the polypeptide against the aggregation induced by stirring;
d) an isotonic,
e) a preservative, chosen for example from the group consisting of phenols, benzyl alcohols, benzothelium halides, and chlorides;
f) water.

If the detergent or the surfactant used is nonionic, it may be chosen from polysorbates, PLURONIC™, polyethylene glycol (PEG) or poloxamers.

An isotonic will make it possible to maintain the isotonicity of the composition and will typically include polyalcohols such as glycerol, erythritol, arabitol, xylitol, sorbitol or mannitol, used alone or in combination. Alternatively, sodium chloride and/or any other inorganic salt may be used as isotonic.

The buffer may be, for example, acetate, citrate, succinate, a phosphate buffer or any other inorganic buffer, depending on the desired pH.

The preservatives of phenol, benzyl alcohol, benzothelium halide and chloride type are known antimicrobial agents. Typical preservatives comprise octadecyldimethylbenzylammonium chloride, hexamethonium chloride, benzalkonium chloride, phenol, butyl or benzyl alcohols, alkyl parabens, such as methyl or propyl paraben, catechol, resorcinol, cyclohexanol, 3-pentanol and m-cresol.

Additional excipients may also comprise antioxidants, such as ascorbic acid and methionine, chelating agents, such as EDTA, sugars, such as sucrose, mannitol, trehalose or sorbitol, etc.

The HIP/PAP protein or the derivative thereof may be in the form of a pharmaceutically acceptable salt. This is intended to mean salts prepared from pharmaceutically acceptable non-toxic acids or pharmaceutically acceptable non-toxic bases, including organic and inorganic salts and acids. By way of example, mention may be made of alkali metal salts (sodium and potassium salts), alkaline-earth metal salts (calcium and magnesium salts), ammonium salts, salts of organic bases (pyridine or triethylamine salts), salts of inorganic acids (hydrochloride, sulfate, nitrate) and salts of organic acids (acetate, oxalate, p-toluenesulfonate).

Modes of Administration of the HIP/PAP Protein:

According to one preferred embodiment, the HIP/PAP protein is administered in an effective amount, i.e. the amount required to obtain the expected effects of the invention. Such an amount of HIP/PAP protein will be determined, generally empirically, according to the pathological condition targeted and to the subject to be treated. The effective amount will also depend on the mode of administration envisioned, on the compound administered (HIP/PAP protein or derivative) and on its formulation. The adjustments required to determine the effective amount for obtaining the maximum therapeutic effect correspond to techniques that are routine for the clinician.

Starting from the results illustrated in the examples, an effective amount of the HIP/PAP protein is between 0.1 μg/day/kg of body weight and approximately 100 mg/day/kg of body weight. Although in certain embodiments an effective amount of the HIP/PAP protein may reach more than 10 mg/kg, an effective amount of the HIP/PAP protein according to the present invention is generally less than 5 mg/kg of body weight, which includes amounts less than 4.5 mg/kg, 4 mg/kg, 3.5 mg/kg, 3 mg/kg, 2.5 mg/kg or 2000 μg/kg. More particularly, an effective amount of the HIP/PAP protein according to the present invention comprises amounts of at least 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 15 μg/kg, 20 μg/kg, 25 μg/kg, 30 μg/kg, 40 μg/kg, 50 μg/kg, 60 μg/kg, 70 μg/kg, 80 μg/kg, 90 μg/kg, 100 μg/kg, 150 μg/kg, 200 μg/kg, 250 μg/kg, 300 μg/kg, 350 μg/kg, 400 μg/kg, 450 μg/kg, 500 μg/kg, 600 μg/kg, 700 μg/kg, 800 μg/kg, 900 μg/kg, 1 mg/kg, 2 mg/kg, 3 mg/kg, 4 mg/kg, 5 mg/kg or more with respect to body weight.

According to particular embodiments, the HIP/PAP protein is administered according to a dosage of between 10 and 5000 μg/kg, preferentially between 100 and 2000 μg/kg.

In mice, an experimentally determined typical effective dose is between 10 and 2000 μg/kg of body weight, more particularly between 150 and 1500 μg/kg of body weight. The inter-species dosage adaptations may be carried out according to a method known from the prior art, for example as described in the article by Mordenti et al., *Pharmaceut. Res.* 8, p. 1351 (1991). Conventionally, in adult mice of normal weight, the effective dose is between 1 and 100 μg/day. Conventionally, in humans, the effective dose of the HIP/PAP protein begins at approximately 3 mg in patients weighing approximately 70 kg, i.e. approximately 40 μg/kg of body weight.

In the pharmaceutical compositions of the present invention for oral, sublingual, subcutaneous, intramuscular, intravenous, topical, local, intratracheal, intranasal, transdermal or rectal administration, the active ingredient (the HIP/PAP protein or one of the derivatives thereof) may be administered in unit administration form as a mixture with pharmaceutical excipients, such as described above and/or conventional, of animals and of human beings, for preventing or treating insulin resistance.

The preferred modes of administration are the enteral, in particular oral, and intravenous routes. By way of example, a composition of the invention may be intravenously administered continuously or by bolus, or orally administered daily.

Advantageously, a combination product according to the invention is administered orally. The appropriate forms for oral administration are, for example, tablets, gel capsules, lozenges, powders, granules, lyophilisates, oral solutes and syrups. Tablets, powders, granules, lyophilisates, oral solutes and syrups constitute the pharmaceutical or cosmetic form suitable for oral administration that is currently preferred. The tablets or gel capsules may be of varied nature, immediate-release, controlled-release or delayed-release, and optionally in effervescent or orodispersible form. A preparation in gel capsules is obtained by mixing the active ingredient (i) or (ii) with a diluent and pouring the mixture obtained into soft or hard gel capsules.

Forms for oral administration, such as gel capsules or tablets, are an advantageous embodiment of the invention. More particularly, the unit administration forms of the HIP/PAP protein, such as gel capsules, tablets, sachets or ampoules for oral suspension, will typically comprise amounts of HIP/PAP protein or of any one of the derivatives thereof ranging from 0.1 to 200 mg and more particularly from 50 to 100 mg.

A preparation in syrup or elixir form may, for example, contain HIP/PAP together with an appropriate sweetener, antiseptic, preservative, flavoring or dye.

The water-dispersible powders, lyophilisates or granules may contain HIP/PAP as a mixture with dispersing agents or wetting agents or suspending agents, and similarly with flavor enhancers or sweeteners.

According to the invention, the HIP/PAP protein, in a form suitable for being taken orally, may also be intended for use as a food supplement. Such a preparation is particularly suitable for the uses in the context of preventing insulin resistance in subjects at risk and/or in undernourished patients, exhibiting a hypercatabolic state, or having sarcopenia. Such a preparation is also suitable for use of HIP/PAP aimed at increasing the lean body mass/fat body mass ratio of individuals.

The HIP/PAP protein may be sterilized prior to the in vivo administration. The sterilization may be obtained by filtration on sterile filtration membranes, before or after the lyophilization or the reconstitution. The systemically administered HIP/PAP protein may advantageously be lyophilized or stored in solution. In lyophilized form, the HIP/PAP protein is generally formulated in combination with excipients which enable reconstitution with an appropriate diluent, at the time of use.

The HIP/PAP protein may be administered daily in one intake or in a fractionated manner (for example from 2 to 3 times per day) until the desired therapeutic effect is obtained. It may also be administered chronically, so as to prevent or limit the development of insulin resistance, for example in subjects at risk, having physiological and/or pathological conditions favorable to the development of insulin resistance.

The HIP/PAP protein may also be administered in the form of a course, for example courses ranging from 15 days to 3 months, optionally repeated from 1 to 6 times at determined doses and time intervals. These modes of administration will be particularly indicated in the context of preventing insulin resistance in subjects at risk and/or in undernourished patients, exhibiting a hypercatabolic state, or having sarcopenia.

The HIP/PAP protein according to the invention may also be combined in the context of a polytherapy with other compounds for treating insulin resistance or the associated conditions, such as dyslipidemia or atherosclerosis.

The HIP/PAP protein according to the invention may also be administered in combination with health and dietary measures, such as a low-calorie and/or low-fat diet and an increase in physical activity.

Use According to the Invention:

The present invention also relates to the use of the HIP/PAP protein or of one of the derivatives thereof, as previously described, for treating, reducing, limiting or preventing the development of insulin resistance, in non-insulin-dependent subjects, as defined in the various embodiments previously described.

According to particular embodiments of the invention, the HIP/PAP protein will be used in the subjects as previously described.

In certain embodiments of the invention, the derivative of the HIP/PAP protein will be characterized in that it comprises an amino acid sequence having a sequence identity of at least 90% with the polypeptide consisting of the amino acid sequence chosen from the sequences SEQ ID No. 1 or SEQ ID No. 2.

FIGURES

FIG. 1A: change in glycemia (mg/dl) during the insulin tolerance test (ITT) in the ob/ob mice after 2 weeks of treatment. FIG. 1B-C: change in insulinemia (ng/ml) during the OGTT (B), and in the HOMA-IR index (C) in the HFD mice after 4 weeks of treatment. FIG. 1D: muscle uptake of glucose in the mice treated for 4 weeks with ALF5755 (white bar) or placebo (black bar).

FIG. 2. A: Effect of the ALF5755 treatment vs placebo on the lean body mass (FIGS. 2B and 2D) and the fat body mass (FIGS. 2A and 2C), the mice having followed an HFD diet (2A, 2C) and control diet (2B, 2D). FIG. 2E-F: [fat body mass/lean body mass] ratio in the mice having followed an HFD diet (2E) or control diet (2F).

FIG. 3. Effect of the ALF5755 treatment (white bar) vs placebo (black bar) on the serum lipid profile in the mice having followed an HFD diet (3A) or control diet (3B). FIG. 3C: serum hepatic assessment in the mice having followed an HFD diet.

EXAMPLES

Materials and Methods:
Animal Models 2 distinct models of insulin resistance and of diabetes were used, the ob/ob model and the High Fat Diet (HFD) model.

The ob/ob model is a genetic model of type II diabetes caused by a nonsense mutation in the leptin gene resulting in an absence of leptin in these animals. This mouse exhibits an insulin-resistance syndrome with hyperinsulinemia, obesity, hyperglycemia and hyperlipidemia (Pelleymounter M A, Cullen M J, Baker M B, Hecht R, Winters D, Boone T, et al. Effects of the obese gene product on body weight regulation in ob/ob mice. *Science* 1995; 269: 540-3). The ob/ob mice exhibit hyperglycemia (248+/−14 mg/dl) and also major hyperinsulinemia (9.5+/−0.9 ng/ml), as conventionally described.

The HFD model is a model of type II diabetes caused by a lipid enrichment of the diet. In a conventional diet (control diet=CTD), the calorie intake is 3200 kcal/kg (21.4% proteins, 5.1% lipids, 47.1% carbohydrates). For the HFD diet, the calorie intake is 4655 kcal/kg (17% proteins, 27.5% lipids, 37.5% carbohydrates). The weight of the HFD animals gradually increases to become significantly different than that of the animals subjected to the control diet, starting from 4 weeks. After 10 weeks of HFD, the average weight of the animals is approximately 30% greater than that of the animals on the control diet. The HFD mice exhibit an insulin-resistance syndrome with hyperinsulinemia, obesity, hyperglycemia and hyperlipidemia (Migrenne S, Lacombe A, Lefevre A L, Pruniaux M P, Guillot E, Galzin A M, Magnan C. Adiponectin is required to mediate rimonabant-induced improvement of insulin sensitivity but not body weight loss in diet-induced obese mice. *Am J Physiol Regul Integr Comp Physiol.* 2009 296(4):929-35.). Ten weeks of HFD diet lead to a significant increase in basal glycemia (220.6±3.7 mg/dl; one-tailed t-test P=0.0001, **) and in basal insulinemia (0.51±0.06 ng/ml; one-tailed t-test P=0.0069, ) compared with the control diet.

The mice subjected to a normal control diet exhibit a basal glycemia (190.4±6.9 mg/dl) and a basal insulinemia (0.29±0.04 ng/ml) and a glycemia and insulinemia during the OGTT test which are normal, and not affected by the administration of ALF-5755 between weeks 10 and 14. For all the experiments, the mice were acclimatized in the animal house by observing a day-night cycle comprising 12 h of illumination (7 am-7 pm).

Treatments
Ob/Ob Model:

29 animals were divided up into 3 groups: 10 animals received placebo (physiological saline), 9 animals received a pump delivering 9 µg/day of ALF5755 and 10 animals received 43 µg/day of ALF5755, for 4 weeks. Delivery was carried out by diffusion from an Alzet pump (Alzet #2004) implanted subcutaneously in the back of the animal and delivering a constant volume subcutaneously at a flow rate of 0.25 µl/hour. The treatment passes into the blood stream and makes it possible to obtain an average serum concentration of ALF5755 (blood hip level) which is zero for the placebo group, 102.7±28.6 ng/ml for the group receiving 9 µg/day of ALF5755 and 229.5±44.9 ng/ml for the group receiving 43 µg/day of ALF5755. For 3 animals of the ALF5755 9 µg/day group and 3 animals of the 43 µg/day group, the delivery of ALF5755 did not take place and the blood hip level was zero at the end of the treatment. These animals were excluded from the analyses. Two animals died during the experiment, one mouse from the control group and one mouse from the ALF5755 43 µg/day group. The numbers retained for each group are therefore: placebo, n=9; ALF5755 9 µg/day, n=6; ALF5755 43 µg/day, n=6.

HFD Model

The animals on HFD and on a control diet are treated with a placebo (physiological saline, n=5 for the CTD group, n=9 for the HFD group) or ALF5755 at 43 µg/day (n=5 for the CTD group, n=9 for the HFD group) for 4 weeks. The delivery is carried out by diffusion from an Alzet pump (Alzet #2004) implanted subcutaneously in the back of the animal and delivering a constant volume subcutaneously at a flow rate of 0.25 µl/hour. The treatment passes into the blood stream and makes it possible to obtain an average serum concentration of ALF5755 (blood hip level) which is zero for the placebo group and 309 ng/ml on D17 for the 2 groups receiving 43 µg/day of ALF5755. On D27 (last day of delivery by the pump), the blood hip levels are 369.3 ng/ml for the animals of the CTD group and 334.8 ng/ml for the HFD group, thus confirming the correct delivery of ALF5755 throughout the treatment.

HFD Model for Tissue Sensitivity (Carbon 14-Labeled Glucose)

The animals on HFD and on the control diet are treated with a placebo (physiological saline, n=4 for the CTD group, n=6 for the HFD group) or ALF5755 at 43 µg/day (n=4 for the CTD group, n=6 for the HFD group) for 4 weeks, according to the same treatment as previously described. The average serum concentration of ALF5755 (blood hip level) is zero for the placebo group, 673 ng/ml for the animals of the CTD group and 784 ng/ml for the HFD group, thus confirming the correct delivery of ALF5755 throughout the treatment.

Variables Studied
Weight

The animals of the HDF experiment are weighed every week during the setting up of the model, and then also for the 4 weeks of treatment in order to validate the weight gain linked to the diet and to evaluate any effect of ALF5755 on this variable.

The ob/ob animals are for their part weighed approximately once a week for the 4 weeks of treatment.
Food Intake for the HFD Experiment The food intake is measured by weighing the food provided and the food remaining 3 times per week. It is then related back to a daily intake (in g/day).
Calorie Intake for the HFD Experiment The calorie intake is directly calculated from the amount of food ingested, in g, and from the energy value per gram of food pellet according to the diet.
Basal Glycemia The animals are made to fast for 18 hours before the various measurements. The basal glycemia is measured using a reader and reactive strips for measuring glycemia in the blood (Glucofix® mio reader and Glucofix® sensor strips, A. Menarini diagnostics). A drop of blood is sufficient for this measurement; it is obtained by taking a blood sample from the end of the tail. The basal glycemia is taken before the implantation of the pumps, after approximately 2 weeks of treatment and then at the end of treatment.
Basal Insulinemia After the basal glycemia measurement, a maximum blood sample of 75 µl is taken using hematocrit capillaries heparinized with sodium 3.75 IU/capillary (Hirschmann Laborgeräte) in order to assay the basal insulinemia. The tubes of blood are centrifuged for 3 minutes at 14 000 rpm, and then the supernatant is removed and stored at −20° C. for the purpose of assaying insulin by ELISA (Ultra Sensitive Mouse Insulin ELISA Kit, Crystal Chem Inc, #90080) according to the manufacturer's recommendations for use.
Oral Glucose Tolerance Test: OGTT After 18 hours of fasting, the animals are weighed and then the basal glycemia and the basal insulinemia are measured. A 30% glucose solution (CDM Lavoisier, 1 L injectable bottle) is then administered by intragastric gavage in a proportion of 2 g/kg of mouse.

The glycemia is measured during a defined time course (between 5 and 90 or 120 minutes after the glucose gavage) in the same way as the basal glycemia.

75 µl of blood are also collected at 15 and 30 minutes in order to assay the insulinemia with a procedure identical to that used for assaying the basal insulinemia.

The HOMA-IR index is calculated from the glycemia and insulinemia values at T0 prior to the administration of glucose, 15 minutes later and 30 minutes later. The HOMA-IR index is calculated according to the following formula:

[(Insulinemia$_{(mU/l)}$×Glycemia)/22.5] if the glycemia is expressed in units of molarity (mmol/l) or

[(Insulinemia$_{(mU/l)}$×Glycemia)/405] if the glycemia is expressed in units of mass (mg/dl).

Subcutaneous Insulin Tolerance Test: ITT

The ob/ob mice are made to fast for a period of 18 h.

A solution of insulin diluted to 0.15 IU/ml in physiological saline, from a stock solution at 100 IU/ml (Novorapid Flexpen 100 IU/ml, NovoNordisk A/S), is injected subcutaneously in a proportion of 0.75 IU/kg of mouse.

The glycemia is measured during a defined time course (between 5 and 120 minutes after the insulin injection) in the same way as previously described.

Tissue Sensitivity to Glucose

In order to know the impact of ALF5755 on the insulin sensitivity of various tissues, 8 µCi of 2-deoxyglucose $^{14}$C (2DG $^{14}$C) are injected intraperitoneally. This is a glucose analog which is not metabolized (it undergoes only the step of phosphorylation by glucokinase) thereby enabling it to accumulate in the tissues. Twenty-five µl of blood are taken at t0, then every 10 minutes for a minimum of 60 minutes, in order to estimate the decrease in 2DG in the blood. The mice are sacrificed by lethal injection of pentobarbital and then the tissues are removed in order to count the radioactivity of the 2DG $^{14}$C taken up.

The tissues are digested in sodium hydroxide at 60° C. for 16 h, and then the solution is neutralized. The samples undergo several quantification steps for the purpose of knowing, on the one hand, the amount of non-phosphorylated 2DG, and, on the other hand, the total amount of 2DG. The amount of 2DG which has actually penetrated into the tissue is calculated by subtraction of these two variables (total 2DG-non-phosphorylated 2DG).

This value, related back to the weight of the tissue, is then divided by the integral of the specific activity of the $^{14}$C in the blood over time (in cpm/mg of glucose) in order to take into account the amount circulating in the blood.

This method makes it possible to demonstrate the specific effect of insulin on glucose transport in an organ, and reflects the insulin sensitivity of this tissue.
MRI for Determination of the Fat Body Mass/Lean Body Mass:

The MRI scan consists in weighing the mouse, then introducing it into a tube and keeping it tightly contained using a pusher. The tube is inserted into the EchoMRI scanner precalibrated with a mouse specific control tube containing a volume defined by the supplier. In 3 minutes, the fat body mass, the lean body mass, the biological fluids and the total free water of the body are quantified.
Hepatic Assessment (ALAT, ASAT, Creatinine, Total Bilirubin):

The serum hepatic assessments are carried out by means of a photometric coloration test using the Olympus AU 400 automated device.
Lipid Assessment (Cholesterol, Cholesterol Ester, Triqlycerides, Neutral Lipids:

The serum and hepatic lipid assessments are carried out by HPLC chromatography.
Results:
Effect of the HIP/PAP Protein on Carbohydrate Homeostasis:

The administration of HIP/PAP significantly decreases the basal glycemia (after 18 hours of fasting) in the HFD mouse (decrease of approximately 15% on day 25 of treatment; 188.9±10.8 in the treated mouse vs. 222.4±8.5 in the placebo mouse, P<0.001, ; two-way ANOVA, treatment effect: $F_{(16.1)}$=12.76, P=0.0025, ), and in the ob/ob mouse, with respect to placebo mouse (decrease of approximately 28% on day 25 of treatment; 228.2±14.7 in the treated mouse, vs. 316.3±32.2 in the placebo mouse, P<0.05, *).

Likewise, the treatment with the HIP/PAP protein also makes it possible to reduce the hyperglycemia during the OGTT test, significantly for the ob/ob model as early as 2 weeks (two-way ANOVA, treatment effect: $F_{(133.1)}$=13.09, P=0.0018, **) and maintained at 4 weeks (two-way ANOVA, treatment effect: $F_{(133.1)}$=5.78, P=0.027, *). For the mice subjected to the HFD diet and treated with HIP/PAP, a tendency toward improvement, which brings the hyperglycemia curve back to a level comparable to that observed in the mice having followed the control diet, is observed.

Figure 1:
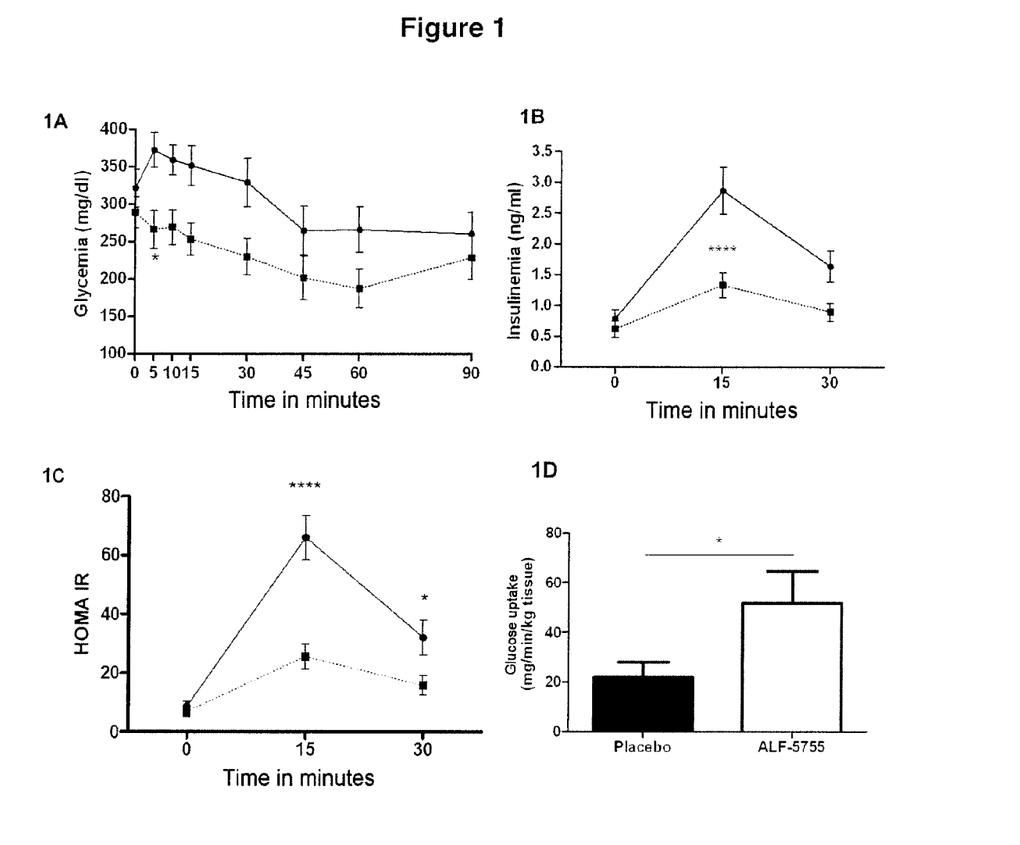
FIG. 1: Effect of the ALF5755 treatment (■) vs placebo (●) on insulin resistance.

The treatment with the HIP/PAP protein also makes it possible to reduce the hyperglycemia during the ITT test, significantly for the ob/ob model at 2 weeks (two-way ANOVA, treatment effect: $F_{(133,1)}=4.71$, P=0.043, *, see FIG. 1A) with a tendency maintained at 4 weeks reflecting a significant and specific improvement in the insulin sensitivity. Indeed, the ITT test consists in lowering the glycemia by injecting exogenous insulin. For the same dose of insulin, the more the glycemia drops in response, the greater the insulin sensitivity (and conversely, the lower the insulin resistance). As illustrated in FIG. 1A, the injection of insulin produces virtually no decrease in the glycemia (at least during the first 30 minutes) in the ob/ob mice having received the placebo treatment. Such an effect reflects a major insulin resistance. Conversely, in the ob/ob mice treated with ALF5755, the injection of insulin leads to a considerable decrease in the glycemia, thus reflecting a considerable decrease in insulin resistance (i.e.: an improvement in insulin sensitivity).

Effect of the HIP/PAP Protein on Insulinemia and the HOMA-IR Index after 1 Month of Treatment:

A decrease in the hyperinsulinemia is observed during the OGTT test in the HFD mice treated with ALF-5755 compared with the mice having received the placebo treatment (decrease in the hyperinsulinemia peak at 15 minutes: 3.75 times the basal level in the treated mouse, vs. 7.61 times in the placebo mouse, P<0.0001, ****, and at 30 minutes: 2.31 times the basal level in the treated mouse, vs. 3.7 times in the placebo mouse, P<0.05, *). These modifications are accompanied by a normalization of the HOMA-IR index in the HFD model: two-way ANOVA, treatment effect: $F_{(32,1)}=16.77$, P=0.0003, ***, see FIG. 1B-C.

In the ob/ob mouse, an improvement in the hyperinsulinemia during the OGTT test is also observed: two-way ANOVA, treatment effect: $F_{(34,1)}=5.84$, P=0.027, *. These modifications are accompanied by a tendency toward normalization of the HOMA-IR index: decrease in the index not statistically significant at 15 and 30 minutes.

All of these data confirm that the normalization of the basal glycemia and of the glycemic excursion during the OGTT test by the treatment with ALF5755 result from the reduction in insulin resistance and not from an insulin-secretagogue effect.

Effect of the HIP/PAP Protein on Tissue Insulin Resistance:

The modulation of the glucose uptake by the various insulin-sensitive tissues (liver, muscles and adipose tissues) after treatment with ALF-5755 was measured in the HFD model by uptake of carbon 14-labeled 2DG. FIG. 1D illustrates that the treatment with ALF5755 leads to an increase in glucose uptake by the muscle (tibialis muscle; 21.7 µM±6.3 versus 51.9 µM±12.8; two-tailed Mann Whitney, P=0.04, *). No increase was observed in the liver or in the adipose tissue.

Figure 2:
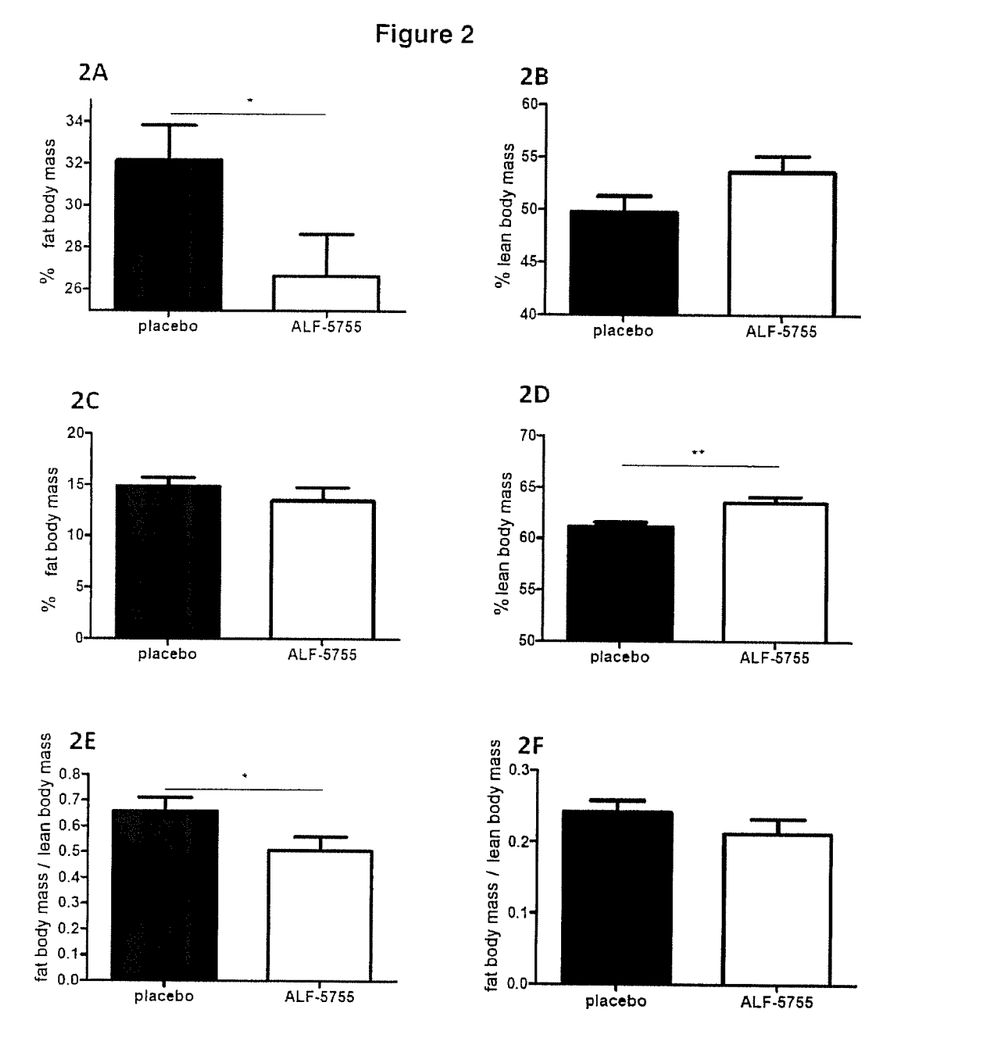

Effect of the HIP/PAP Protein on the Fat Body Mass and Lean Body Mass Percentages:

The 14 weeks of HFD diet induce a considerable increase in the fat body mass percentage (FIGS. 2A and C: 32% versus 15% in the control diet for the placebo groups). The treatment with ALF-5755 significantly decreases the increase in fat body mass observed in the animals subjected to the HFD (FIG. 2A: 32.1%±1.7% versus 26.7%±2.0%; one-tailed Mann Whitney test: P=0.039, *). A comparable trend is observed for the mice subjected to the control regime. Similarly, a decrease in the lean body mass is observed in the group of animals on HFD compared to the control diet (FIGS. 2B and D: 49.8% versus 61.2% in the control diet for the placebo groups). The treatment with ALF-5755 significantly increases the lean body mass percentage observed in the animals subjected to the CTD (FIG. 2D: 61.2%±0.4% versus 63.5%±0.6%; one-tailed Mann Whitney test: P=0.008, **). A comparable trend is observed for the mice subjected to the HFD diet. The analysis of the fat body mass/lean body mass ratio shows that the treatment with ALF-5755 leads to a significant decrease of at least 20% (21%) in this ratio in the mice having followed the HFD diet (Mann-Whitney one-tailed test, P=0.047) and also a tendency toward a decrease of at least 10% (10.1%) in the mice subjected to the control diet, with respect to the mice having received a placebo treatment.

Effect of the HIP/PAP Protein on the Serum and Hepatic Lipid Profiles:

In the groups of HFD animals (see FIG. 3A), it is observed that ALF-5755 leads to a statistically significant decrease in the cholesterol level (913.0 µM±28.2 versus 647.1 µM±32.9; two-tailed Mann Whitney, P<0.0001, ****), in the cholesterol ester level (1760.6 µM±65.8 versus 1390.3 µM±96.7; two-tailed Mann Whitney Whitney, P=0.011, *), and in the total neutral lipid level (2834.9 µM±95.9 versus 2168.6 µM±118.5; two-tailed Mann Whitney, P=0.0005, ***), and a tendency toward a decrease in the triglyceride level (161.3 µM±15.0 versus 131.2 µM±24.1).

Comparable and statistically significant effects are observed with the treatment with ALF-5755 in the control diet (FIG. 3B) for cholesterol (526.6 µM±35.9 versus 376.9 µM±43.9; two-tailed Mann Whitney, P=0.032, *), and for the triglycerides (323.2 µM±72.6 versus 143.0 µM±31.5; two-tailed Mann Whitney, P=0.016, *).

In the ob/ob model (FIG. 3C), ALF-5755 decreases cholesterol (763.0 µM±58.5 versus 532.5 µM±29.0; two-tailed Mann Whitney, P=0.002, **), and a tendency toward a decrease in the triglyceride level is observed (651.7 µM±168.6 versus 271.8 µM±44.6).

Figure 3:
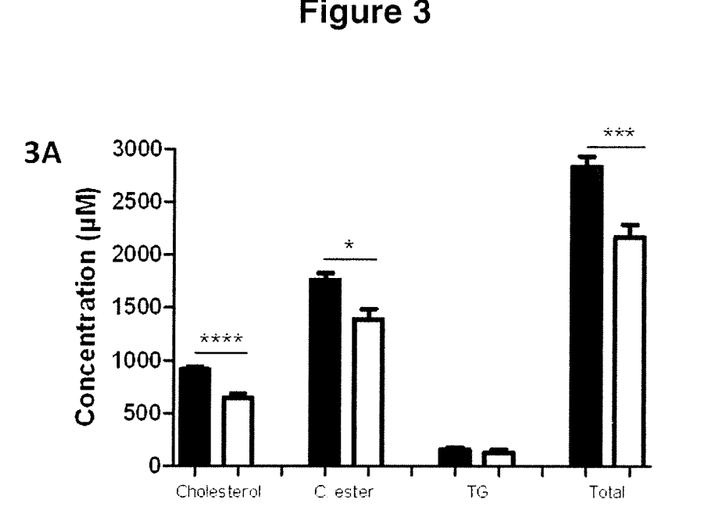

A tendency toward a decrease in ASATs and a statistically significant decrease in ALATs are also observed in the HFD mice treated with ALF-5755 (132.7 µM±19.3 versus 77.2 µM±12.7; two-tailed Mann Whitney, P=0.032, *, see FIG. 3C). Furthermore, comparable tendencies are observed in the control diet and in the ob/ob mouse model.

The invention claimed is:

1. A method for treating insulin resistance in a non-insulin-dependent subject having a carbohydrate homeostasis disorder and a normal fasting glycemia, comprising administering a HIP/PAP protein, or a derivative thereof, to said subject, wherein said derivative comprises an amino acid sequence having a sequence identity of at least 90% with a polypeptide amino acid sequence selected from the group consisting of SEQ ID Nos 1 to 4.

2. The method according to claim 1, wherein the subject has a HOMA-B value greater than or equal to 60% and/or a HOMA-IR index of less than 6.

3. The method according to claim 1, wherein the subject has a fasting glycemia of less than 125 mg/dl.

4. The method according to claim 1, wherein the subject has a glycemia, 2 h after an oral glucose tolerance test, of less than 200 mg/dl.

5. The method according to claim 1, wherein the subject has a normal carbohydrate tolerance.

6. The method according to claim 1, wherein the subject has at least one of the disorders selected from the group consisting of: visceral excess weight, obesity, hyperandrogenism, an eating disorder, sarcopenia, hypercatabolism, and undernourishment.

7. The method according to claim 1, wherein the insulin resistance is associated with aging.

8. The method according to claim 1, wherein the step of administering results in increasing muscle development, stimulating increased lean body mass and preventing or limiting muscle catabolism and protein undernourishment.

9. The method according to claim 1, wherein the step of administering results in preventing or treating dyslipidemia.

10. The method according to claim 1, wherein the step of administering results in preventing or treating atherosclerosis.

11. A method for treating insulin resistance in a non-insulin-dependent subject having a carbohydrate homeostasis disorder and a normal fasting glycemia, comprising administering a composition comprising an effective amount of the HIP/PAP protein or a derivative thereof, as a mixture with at least one physiologically acceptable excipient, wherein said derivative comprises an amino acid sequence having a sequence identity of at least 90% with a polypeptide amino acid sequence selected from the group consisting of SEQ ID Nos 1 to 4.

12. The method of claim 3, wherein said fasting glycemia is less than 110 mg/dl.

13. The method of claim 4, wherein said glycemia is less than 140 mg/dl.

14. The method of claim 9, wherein said dyslipidemia is hypercholesterolemia.

15. The method of claim 10, wherein said atherosclerosis is coronary artery disease and/or arteriopathy of the lower limbs.

* * * * *

SEQUENCE LISTING

<160> NUMBER OF SEQ ID NOS: 4

<210> SEQ ID NO 1
<211> LENGTH: 149
<212> TYPE: PRT
<213> ORGANISM: Homo sapiens

<400> SEQUENCE: 1

Glu Glu Pro Gln Arg Glu Leu Pro Ser Ala Arg Ile Arg Cys Pro Lys
1               5                   10                  15

Gly Ser Lys Ala Tyr Gly Ser His Cys Tyr Ala Leu Phe Leu Ser Pro
            20                  25                  30

Lys Ser Trp Thr Asp Ala Asp Leu Ala Cys Gln Lys Arg Pro Ser Gly
        35                  40                  45

Asn Leu Val Ser Val Leu Ser Gly Ala Glu Gly Ser Phe Val Ser Ser
    50                  55                  60

Leu Val Lys Ser Ile Gly Asn Ser Tyr Ser Tyr Val Trp Ile Gly Leu
65                  70                  75                  80

His Asp Pro Thr Gln Gly Thr Glu Pro Asn Gly Glu Gly Trp Glu Trp
                85                  90                  95

Ser Ser Ser Asp Val Met Asn Tyr Phe Ala Trp Glu Arg Asn Pro Ser
            100                 105                 110

Thr Ile Ser Ser Pro Gly His Cys Ala Ser Leu Ser Arg Ser Thr Ala
        115                 120                 125

Phe Leu Arg Trp Lys Asp Tyr Asn Cys Asn Val Arg Leu Pro Tyr Val
    130                 135                 140

Cys Lys Phe Thr Asp
145

<210> SEQ ID NO 2
<211> LENGTH: 138
<212> TYPE: PRT
<213> ORGANISM: Homo sapiens

<400> SEQUENCE: 2

Ile Arg Cys Pro Lys Gly Ser Lys Ala Tyr Gly Ser His Cys Tyr Ala
1               5                   10                  15

Leu Phe Leu Ser Pro Lys Ser Trp Thr Asp Ala Asp Leu Ala Cys Gln
            20                  25                  30

Lys Arg Pro Ser Gly Asn Leu Val Ser Val Leu Ser Gly Ala Glu Gly
        35                  40                  45

Ser Phe Val Ser Ser Leu Val Lys Ser Ile Gly Asn Ser Tyr Ser Tyr
    50                  55                  60

Val Trp Ile Gly Leu His Asp Pro Thr Gln Gly Thr Glu Pro Asn Gly
65                  70                  75                  80

Glu Gly Trp Glu Trp Ser Ser Ser Asp Val Met Asn Tyr Phe Ala Trp
                85                  90                  95

Glu Arg Asn Pro Ser Thr Ile Ser Ser Pro Gly His Cys Ala Ser Leu
            100                 105                 110

Ser Arg Ser Thr Ala Phe Leu Arg Trp Lys Asp Tyr Asn Cys Asn Val
        115                 120                 125

Arg Leu Pro Tyr Val Cys Lys Phe Thr Asp
    130                 135

<210> SEQ ID NO 3
<211> LENGTH: 150
<212> TYPE: PRT
<213> ORGANISM: Homo sapiens

<400> SEQUENCE: 3

Met Glu Glu Pro Gln Arg Glu Leu Pro Ser Ala Arg Ile Arg Cys Pro
1               5                   10                  15

Lys Gly Ser Lys Ala Tyr Gly Ser His Cys Tyr Ala Leu Phe Leu Ser

```
                        20                  25                  30
Pro Lys Ser Trp Thr Asp Ala Asp Leu Ala Cys Gln Lys Arg Pro Ser
        35                  40                  45
Gly Asn Leu Val Ser Val Leu Ser Gly Ala Glu Gly Ser Phe Val Ser
        50                  55                  60
Ser Leu Val Lys Ser Ile Gly Asn Ser Tyr Ser Tyr Val Trp Ile Gly
65                  70                  75                  80
Leu His Asp Pro Thr Gln Gly Thr Glu Pro Asn Gly Glu Gly Trp Glu
                85                  90                  95
Trp Ser Ser Ser Asp Val Met Asn Tyr Phe Ala Trp Glu Arg Asn Pro
                100                 105                 110
Ser Thr Ile Ser Ser Pro Gly His Cys Ala Ser Leu Ser Arg Ser Thr
                115                 120                 125
Ala Phe Leu Arg Trp Lys Asp Tyr Asn Cys Asn Val Arg Leu Pro Tyr
                130                 135                 140
Val Cys Lys Phe Thr Asp
145                 150

<210> SEQ ID NO 4
<211> LENGTH: 175
<212> TYPE: PRT
<213> ORGANISM: Homo sapiens

<400> SEQUENCE: 4

Met Leu Pro Pro Met Ala Leu Pro Ser Val Ser Trp Met Leu Leu Ser
1               5                   10                  15
Cys Leu Met Leu Leu Ser Gln Val Gln Gly Glu Glu Pro Gln Arg Glu
                20                  25                  30
Leu Pro Ser Ala Arg Ile Arg Cys Pro Lys Gly Ser Lys Ala Tyr Gly
                35                  40                  45
Ser His Cys Tyr Ala Leu Phe Leu Ser Pro Lys Ser Trp Thr Asp Ala
                50                  55                  60
Asp Leu Ala Cys Gln Lys Arg Pro Ser Gly Asn Leu Val Ser Val Leu
65                  70                  75                  80
Ser Gly Ala Glu Gly Ser Phe Val Ser Ser Leu Val Lys Ser Ile Gly
                85                  90                  95
Asn Ser Tyr Ser Tyr Val Trp Ile Gly Leu His Asp Pro Thr Gln Gly
                100                 105                 110
Thr Glu Pro Asn Gly Glu Gly Trp Glu Trp Ser Ser Ser Asp Val Met
                115                 120                 125
Asn Tyr Phe Ala Trp Glu Arg Asn Pro Ser Thr Ile Ser Ser Pro Gly
                130                 135                 140
His Cys Ala Ser Leu Ser Arg Ser Thr Ala Phe Leu Arg Trp Lys Asp
145                 150                 155                 160
Tyr Asn Cys Asn Val Arg Leu Pro Tyr Val Cys Lys Phe Thr Asp
                165                 170                 175
```